(12) United States Patent
Stiles et al.

(10) Patent No.: US 9,066,521 B2
(45) Date of Patent: Jun. 30, 2015

(54) ENHANCED PRESERVATION OF PROCESSED FOOD

(75) Inventors: Michael E. Stiles, Edmonton (CA); Denise Carlson, Edmonton (CA); David C. Smith, Toronto (CA)

(73) Assignee: GRIFFITH LABORATORIES, INC., Alsip, IL (US)

( * ) Notice: Subject to any disclaimer, the term of this patent is extended or adjusted under 35 U.S.C. 154(b) by 1428 days.

(21) Appl. No.: 12/282,431

(22) PCT Filed: Mar. 23, 2007

(86) PCT No.: PCT/CA2007/000444
§ 371 (c)(1),
(2), (4) Date: Mar. 7, 2011

(87) PCT Pub. No.: WO2007/106993
PCT Pub. Date: Sep. 27, 2007

(65) Prior Publication Data
US 2012/0064210 A1    Mar. 15, 2012

Related U.S. Application Data

(63) Continuation of application No. 11/013,929, filed on Dec. 17, 2004.

(60) Provisional application No. 60/785,119, filed on Mar. 23, 2006.

(51) Int. Cl.
| | | |
|---|---|---|
| *A23L 3/3463* | (2006.01) |
| *A01N 63/00* | (2006.01) |
| *A01N 63/02* | (2006.01) |
| *A23B 4/20* | (2006.01) |
| *A23B 4/22* | (2006.01) |
| *A23L 3/3508* | (2006.01) |
| *A23L 3/3571* | (2006.01) |
| *C12N 1/20* | (2006.01) |
| *C12R 1/01* | (2006.01) |

(52) U.S. Cl.
CPC ............... *A01N 63/00* (2013.01); *A01N 63/02* (2013.01); *A23B 4/20* (2013.01); *A23B 4/22* (2013.01); *A23L 3/3463* (2013.01); *A23L 3/34635* (2013.01); *A23L 3/3508* (2013.01); *A23L 3/3571* (2013.01); *C12N 1/20* (2013.01); *C12R 1/01* (2013.01)

(58) Field of Classification Search
CPC ....... A01N 63/00; A01N 63/02; A01N 37/36; A01N 37/42; A01N 2300/00; A23B 4/20; A23B 4/22; A23L 3/34635; A23L 3/3508; A23L 3/3571; A23L 3/3463; C12R 1/01; C12N 1/20
USPC ................. 426/335, 532, 654; 424/93.4, 115; 514/2.4
See application file for complete search history.

(56) References Cited

U.S. PATENT DOCUMENTS

| 6,991,820 B2 | 1/2006 | Ming et al. |
| 2003/0108648 A1 * | 6/2003 | Ming et al. .................... 426/532 |

FOREIGN PATENT DOCUMENTS

| CA | 2430095 A1 | 11/2003 |
| CA | 2432907 A1 | 12/2004 |
| EP | 0466244 A1 | 1/1992 |

* cited by examiner

*Primary Examiner* — Leslie Wong
(74) *Attorney, Agent, or Firm* — Drinker Biddle & Reath LLP

(57) ABSTRACT

The present invention included compositions and methods for treating *Listeria* in foods. The compositions and methods include at least one first preservative, and a second preservative selected from the group consisting of a *Carnobacterium* species, *Carnobacterium maltaromaticum*, a fermentate, containing at least one bacteriocin, and combinations thereof.

11 Claims, 5 Drawing Sheets

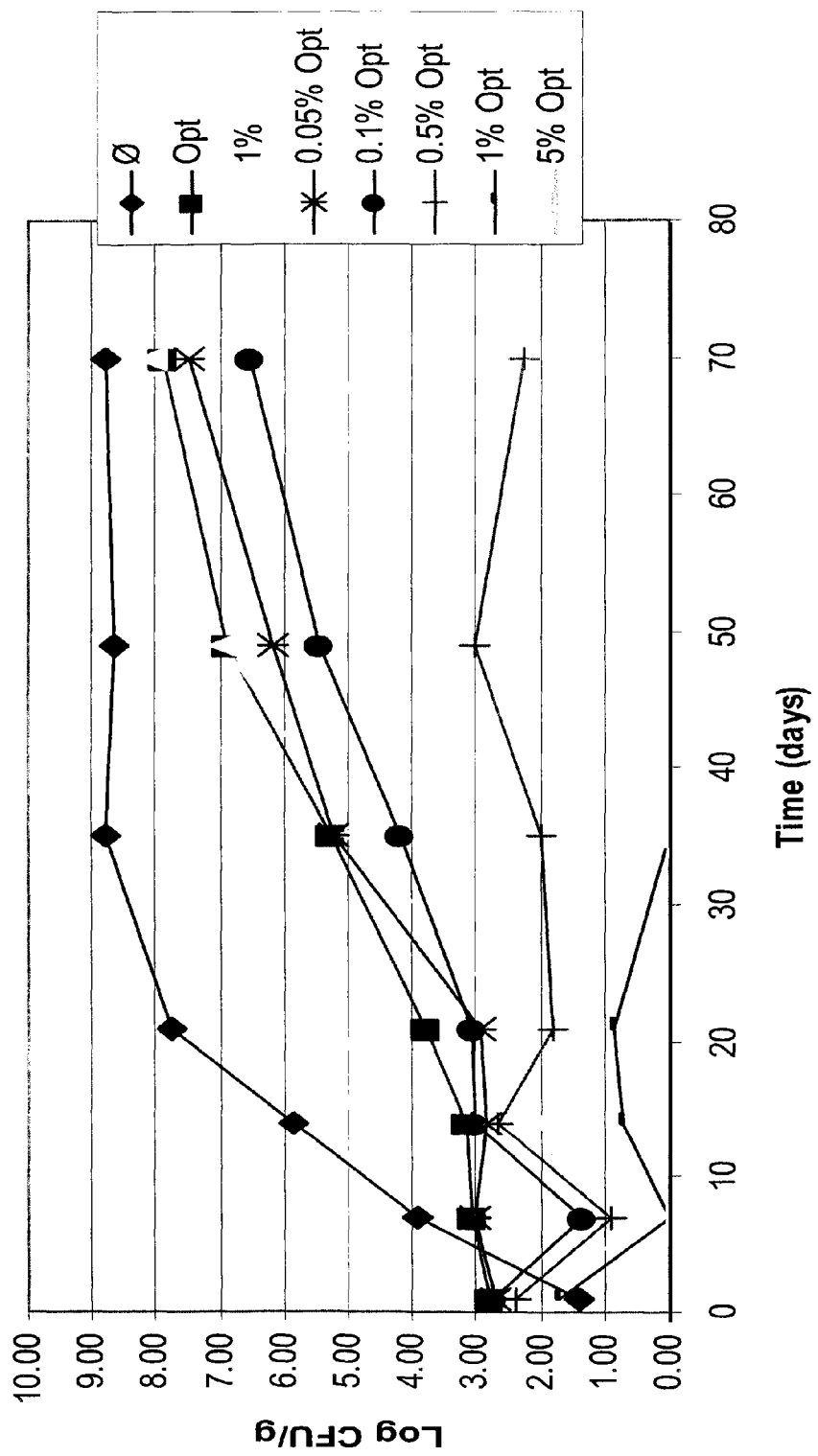

ENHANCED PRESERVATION OF PROCESSED FOOD

The present invention claims priority from U.S. Ser. No. 60/785,119, filed 23 Mar. 2006, and is a continuation-in-part of U.S. Ser. No. 11/013,929, filed 17 Dec. 2004.

I. FIELD OF INVENTION

This invention relates to methods and compositions for preserving food and food products, particularly processed meats, from microorganism contamination or spoilage, specifically to prevent growth of Listeria monocytogenes. This invention also relates to novel strains of Carnobacterium maltaromaticum that produce bacteriocin molecules having antimicrobial activity. The bacteria of the present invention, and the bacteriocin(s) produced by the bacteria or other bacteria, may be used to treat food and as a food preservative. In a particular application of the invention, the bacteriocin and the bacterial strain that produces the bacteriocin are used to control pathogenic bacteria, including but not limited to, Listeria monocytogenes ("L. monocytogenes") in meat products, without jeopardizing the storage life of the meats.

II. BACKGROUND OF THE INVENTION

In the United States a mixture of sodium lactate (NaL) and/or potassium lactate and sodium diacetate (NaAc) is known as a method to prevent growth of Listeria monocytogenes in processed meats. It is also known to treat processed food, to use NaL or NaL/NaAc in combination with Nisin (a bacteriocin derived from Lactococcus lactis), Microgard (a Propionii), and Alta 2341 (a commercially available fermentation product of Pediococcus acidilactici).

Carnobacterium maltaromaticum is one species of a diverse group of bacteria that are classified as Lactic Acid Bacteria (LAB). LAB have been utilized for centuries in the food and dairy industries in the production of fermented foods. Important in this capacity is their ability to produce aromatic and flavor-enhancing compounds (Stiles and Holzapfel, 1997; Carr et al., 2002). LAB have been characterized by their ability to produce a variety of isomers of lactic acid from the fermentation of carbohydrates. Carnobacteria are distinct from Lactobacilli due their inability to grow on acetate agar at pH 5.6, while being able to produce virtually pure L(+)-lactic acid from glucose, and in their ability to ferment both glycerol and mannitol, properties that are unusual in lactobacilli (Holzapfel and Gerber, 1983; Shaw and Harding, 1984).

One of the methods by which C. maltaromaticum may inhibit potentially pathogenic bacteria is through the production of bacteriocins. Bacteriocins are ribosomally synthesized, low molecular weight antibacterial proteinaceous materials that are able to kill closely related bacteria (Klaenhammer, 1993). Bacteriocins have been shown to be produced by LAB isolated from beef, spoiled ham, as well as from French mold-ripened soft cheese (Jack et al., 1996; Herbin et al., 1997). Because bacteriocins are isolated from LAB from foods such as meat and dairy products, both LAB and bacteriocins have been consumed for centuries. The inhibitory substances produced from C. maltaromaticum have been shown to be bacteriocins by their susceptibility to proteolytic enzymes.

There is a continual need for new food preservatives bearing new and useful properties. Further, there is growing interest in replacing traditional "chemical" food preservatives with effective "natural" preservatives, especially those that inhibit pathogenic microorganisms. In this regard, considerable research has been conducted on bacterial peptides, e.g., bacteriocins, which are often heat stable and have antimicrobial activity.

Notwithstanding the usefulness of the above-described methods, a need still exists for enhanced preservation of processed food to control the growth and/or to eliminate bacterial contamination, particularly L. monocytogenes.

III. SUMMARY OF THE INVENTION

This invention relates to the use of novel strains of bacteriocin-producing Carnobacterium maltaromaticum ("C. maltaromaticum"), previously known as Carnobacterium piscicola ("C. piscicola"), having exceptional antimicrobial activities, in combination with other food preservatives. The novel strains of the present invention, CB1, CB2, and CB3 produce multiple bacteriocins, including carnobacteriocin BM1 and piscicolin 126. These bacteriocins have broad spectrum anti-Listerial activity, and the producer strains grow at refrigeration temperatures and do not cause food spoilage relative to other similarly related spoilage microorganisms or within the typical shelf-life of the food. In combination, these two types of preservatives provide unexpected and unprecedented anti-bacterial activity.

This invention comprises the method of combining a preservative of the present invention with existing preservation techniques or compounds as identified above to food products. Some methods include adding the two preservatives to the food ingredients prior to cooking, e.g., to a food batter; some methods include applying the preservative of the present invention to the food after cooking, e.g., by spraying. These methods have been shown to improve the effectiveness in inhibiting L. monocytogenes on processed foods unexpectedly beyond the use of either treatment alone.

An advantage of the invention is unprecedented anti-listerial activity. Such activity is exceptional. Another advantage of the invention is that there is both bactericidal and bacteriostatic potential. Yet another advantage of the invention is that these bacteria grow at temperatures as low as 0° C., indicating that they grow and are effective under the refrigeration temperatures that are essential for the preservation of meats. Yet a further advantage of the invention is that these strains, in and of themselves, do not cause significant spoilage of the meats.

This invention provides the addition of a first preservative and a second preservative to a food or food ingredient(s), said second preservative comprising a dried preparation of Carnobacterium maltaromaticum CB1 and its dried fermentate, or the dried fermentate alone (i.e., no live cells). In accordance with the present invention, the combination of these two preservation techniques provides an enhanced inhibition of L. monocytogenes. We also determined that in combination with a second preservative in accordance with the present invention, L. monocytogenes could be inhibited at a commercial level of NaL+NaAc, or one-half of that level. Use of NaL/NaAc in combination with this second preservative has a markedly improved effect of reducing the numbers of Listeria monocytogenes that could be detected on a processed meat product.

IV. BRIEF DESCRIPTION OF THE DRAWINGS

FIG. 1 compares the efficacy of sodium lactate (Galaflow™) to a second preservative of the present invention.

FIG. 2 compares the efficacy of a sodium lactate/sodium acetate mixture (Optiform™) to a second preservative of the present invention.

FIG. 3 compares the efficacy of pediocin (Alta™ 2341) to a second preservative of the present invention.

FIG. 5 shows the results of the experiments described in Example 5.

V. DETAILED DESCRIPTION OF THE INVENTION

Figure 1:
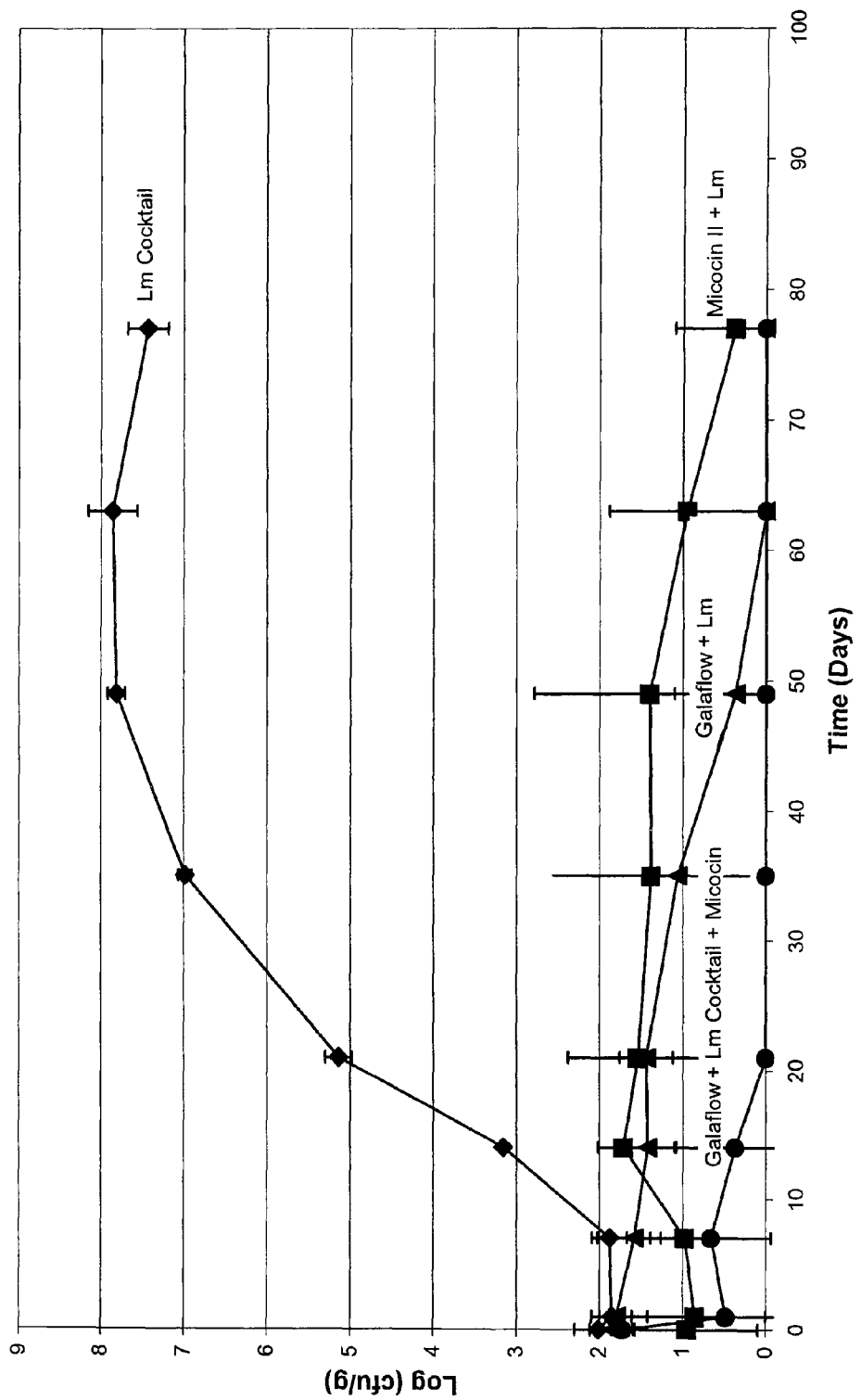

The present invention is methods and compositions for improving food and beverage preservation by applying to the food a first preservative and a second preservative. The first preservative is a conventional chemical preservative, such as one or more acidulants; the second preservative comprises one or more of the following: at least one *Carnobacterium* species; a fermentate containing at least one bacteriocin; a fermentate containing at least one bacteriocin produced by a *Carnobacterium* species; a fermentate derived from a *Carnobacterium* species; one or more partially or wholly purified bacteriocins; one or more partially or wholly purified bacteriocins produced by one or more *Carnobacterium* species; and combinations thereof.

The present invention includes compositions and methods for inhibiting *Listeria*, wherein a first preservative is combined with an effective amount of a second preservative, said second preservative comprising a composition containing at least one ingredient from the group consisting of a bacteriocin(s), bacteriocin(s) produced by a *Carnobacterium*, one or more *Carnobacterium* strains, a fermentate containing bacteriocin(s), a fermentate containing a bacteriocin produced by a *Carnobacterium*, and combinations thereof. In preferred embodiments of the invention, the second preservative includes at least one *Carnobacterium* species and a fermentate produced by said *Carnobacterium* species, or the fermentate alone.

The present invention includes compositions and methods comprising a mixture of 1) a first preservative; and 2) a second preservative comprising a *Carnobacterium* and/or its fermentate, said fermentate comprising at least one bacteriocin that effectively prevents growth of *Listeria monocytogenes*. The compositions and methods of the present invention may be used in connection with the production, packaging, and storage of food and food products, and the cleaning of equipment used therefore. The compositions and methods of the present invention may be used in connection with the producing, preserving, treating and storing food and food products.

The compositions and methods of the present invention may be used in inhibiting the growth of *L. monocytogenes* in food and food products.

In accordance with some embodiments of the invention, it may be desirable to add a first preservative and a second preservative to a food or one of its ingredients prior to cooking. In these embodiments of the invention, the second preservative typically comprises at least one fermentate (and optionally at least one *Carnobacterium* strain).

In accordance with other embodiments of the invention, it may be desirable to contact a surface of a food after processing or cooking. In these embodiments of the invention, the second preservative typically comprises at least one *Carnobacterium* strain and at least one fermentate.

As used herein, a first preservative refers to any preservative, typically a preservative suitable for use with a food, food product, or ingredient of a food product. Exemplary preservatives include but are not limited to a lactate and/or diacetate containing preservative, and mixtures thereof. Typical lactate preservatives include, but are not limited to sodium and potassium lactate. Typical acetate preservatives include, but are not limited to sodium diacetate. Examples of such first preservatives are commercially available under the tradenames Galaflow (a sodium lactate), Optiform (a sodium lactate and sodium diacetate mixture), and Purasal (lactates available from Purac). These preservatives may be used in any amount known to those skilled in the art, typically in an amount taught by the vendors of such products.

As used herein, a second preservative refers to any preservative that contains at least one strain of bacteriocin producing bacteria and/or a composition comprising a fermentate containing one or more bacteriocins. Exemplary second preservatives include but are not limited to at least one *Carnobacterium* species; a fermentate containing at least one bacteriocin; a fermentate containing at least one bacteriocin produced by a *Carnobacterium* species; a fermentate derived from a *Carnobacterium* species; one or more partially or wholly purified bacteriocins; one or more partially or wholly purified bacteriocins produced by or obtained from a *Carnobacterium* species; and combinations thereof.

As used herein, *Carnobacterium* refers to any *Carnobacterium* species that produces one or more bacteriocins. The bacteriocin may be produced naturally or may be a product of genetic modification. In preferred embodiments of the invention, the *Carnobacterium* species is *Carnobacterium maltaromaticum*. In some embodiments of the invention, the *Carnobacterium maltaromaticum* species is the CB1 isolate. In the most preferred embodiments of the invention, the *Carnobacterium maltaromaticum* species is CB1, deposited in the American Type Culture Collection (10801 University Boulevard, Manassas, Va. USA 20118) on 9 Jul. 2003, and received Accession No. PTA-5313. In another exemplary embodiment, the present invention comprises a culture of bacterial strain CB2. CB2 was deposited in the American Type Culture Collection (10801 University Boulevard, Manassas, Va. USA 20118) on 9 Jul. 2003, and received Accession No. PTA-5314. In another exemplary embodiment, the present invention comprises a culture of bacterial strain CB3. CB3 was deposited in the American Type Culture Collection (10801 University Boulevard, Manassas, Va. USA 20118) on 9 Jul. 2003, and received Accession No. PTA-5315.

In another exemplary embodiment, the present invention comprises the use of a first preservative and a second preservative for the treatment of food, for the treatment of spoilage bacteria on food, for the treatment of pathogenic bacteria on food, and/or establishes a predictable storage life for a food or food product. Strains CB1, CB2, and/or CB3 may be used alone or in combination; may be used with or without their respective bacteriocins; may be used with or without a fermentate comprising their respective bacteriocins; may be used in combination with one or more bacteriocin-producing bacteria, including but not limited to a lactic acid bacterium; and/or may be used with one or more bacteriocins produced from a different bacterium; and/or may be used with or without a fermentate comprising one or more bacteriocins produced from a different bacterium.

Another exemplary embodiment of the present invention includes a mixture of 1) a first preservative; and 2) a second preservative comprising a *Carnobacterium* and its fermentate, said fermentate comprising at least one bacteriocin that effectively prevents growth of *Listeria monocytogenes*, wherein the mixture is added to the food product "meat batter" prior to processing.

As used herein, effective amount refers to any dosage or amount suitable for inhibiting bacteria, preferably a *Listeria* species, more preferably *Listeria monocytogenes*. This amount may be bacteriostatic or bactericidal. One skilled in the art will readily recognize or can easily determine an effective amount. For the second preservative, the inventors have found that an amount of $10^2$, or less, colony forming units ("cfu") per gram or per cm$^2$ is typically not sufficient to compete with the existing adventitious microbial population. The inventors have found that 10-fold greater than the initial background microflora, typically about $10^3$ cfu per gram or per cm$^2$ or greater, is sufficient to overcome the growth of the existing adventitious bacterial (e.g., background microflora) population. One skilled in the art will recognize that the amount of adventitious bacteria in a food product is variable. In accordance with the present invention, the amount of the composition should be about ten times or more higher than the amount of adventitious bacteria.

An effective amount of a second preservative refers to an amount sufficient to be bacteriostatic or bacteriocidal. One skilled in the art will recognize that the amount or concentration may vary with the type of food and when it is applied to the food, among other considerations. For example, the inventors have found that up to about 10% by weight may be added to pre-processed ingredients, e.g., to a food batter. For example, a range from about 0.05% to about 5% by weight has been found to be effective as a preservative without unduly affecting other food characteristics, such as taste.

One skilled in the art will also recognize that the concentration of each individual preservative need not be bacteriostatic or bactericidal. In accordance with the present invention, the mixture or combined effect of the two preservatives should be sufficient to inhibit a bacterium such as *Listeria*. The bacteriostatically or bacteriocidally optimum effective amount to be used will depend on the composition of the particular food product to be treated and the method used for applying the composition to the food surface, but can be determined by simple experimentation.

An embodiment of the present invention comprises concentration ranges of the mixture prior to processing suitable for inhibiting *Listeria* species, notably *Listeria monocytogenes*. This amount may be bacteriostatic or bactericidal. The ranges may differ based on the combination of mixtures, i.e., CB1 and fermentate, CB1, another bacteriocin, and fermentate, etc. One skilled in the art will readily recognize or can easily determine an effective amount.

As used herein, fermentate refers to the use of a fermentation product of one or more natural bacterial cultures, homologous pasteurized or unpasteurized fermentate, heterologous pasteurized or unpasteurized fermentate or combinations thereof. The natural bacterial cultures of the present invention are described above. A homologous fermentate refers to the culture supernatant of a single bacterial culture prepared according to standard preparation techniques. A heterologous fermentate refers to the culture supernatant derived from a different bacterial culture prepared according to standard preparation techniques. The homologous or heterologous fermentate may be i) pasteurized or unpasteurized; ii) lyophilized; or iii) otherwise dried. Two or more bacterial cultures may be mixed or added separately. Two or more fermentates may be mixed or added separately. A bacterial culture combined with one or more fermentates may be mixed, or added sequentially. Fermentate also includes one or more partially or wholly purified active ingredients produced by a bacterium, e.g., bacteriocins.

As used herein, bacteriocin is used in its conventional definition, typically referring to one or more substances produced by a first bacterium and effective against a one or more second bacterium. Bacteriocins, which are antibacterial peptides and proteins produced by bacteria including LAB as normal by-products of their metabolism, are potentially very attractive natural preservatives. Many LAB are well-established, industrially important bacteria that include *Streptococcus thermophilus* and species of the genera *Lactococcus, Pediococcus, Leuconostoc, Lactobacillus* and *Carnobacterium*. They have been used for the production of fermented foods that have been consumed safely for thousands of years. Because they have achieved a status as "safe" microorganisms, they are a particularly suitable source of natural antimicrobials, such as bacteriocins, and for use in foods.

Bacteriocins can have a broad or narrow spectrum of antibacterial activity, and are not lethal to the cells that produce them. Bacteria protect themselves from the lethal effects of their own bacteriocins by the production of immunity proteins.

An important aspect of the present invention comprises the use of the bacterial fermentate in the preparation, the preservation, and treatment of a food, preferably a processed food. In accordance with the teachings of the present invention, the bacteriocins produced by strains CB1, CB2, or CB3 appear to act favorably (possibly synergistically) to provide greater protection and effectiveness than use of the individual bacteriocins alone.

The antimicrobial preservatives of the present invention may be used in connection with any food product which is susceptible to microbial degradation, or at any stage of processing that results in a food or food product.

"Food," "food product," "ingredient(s)," "batter," "Fresh," and "processed" are intended to be used in their ordinary meaning as known to those skilled in the art.

The preservatives of the present invention may be added, alone or in combination, serially or sequentially, to any recipe, food ingredient or ingredients, or food substance for which inhibition of food spoilage and/or foodborne pathogens is desired, including raw foods and foods which are partially or fully processed, cured or fermented prior to the addition of the preservatives of the present invention.

For example, the preservatives may be added to an unprocessed edible food substances including raw vegetables such as lettuce, cabbage or carrots, beef, fish, seafood, and other raw foods; a non-fermented, processed food substance including meat products such as hot dogs or frankfurters, bologna and other luncheon meats; a fermented processed food substance such as sausage or sauerkraut; or a cured processed food substance such as ham. The food substance may also be a milk-based or cream-based food, such as ice cream or cottage cream.

The use of the term "food surface" is defined to include any and all internal or external surfaces of the food product being treated. A composition according to the present invention is most readily used by applying it on the exterior surface of a blended food product, such as a hot dog or bologna, or of a solid food, such as a piece of roasted beef, so as to minimize loss of activity in the fat phase of the food. A composition may alternatively be included in the emulsion or raw ingredients of a food, such as batters, sauces, or salsas, or to the interior of solid products, such as hams, by spraying, injecting, or tumbling. In still other embodiments, the composition may be applied as a marinade, breading, seasoning rub, glaze, colorant mixture, and the like, the key criteria being that the antimicrobial composition be available to the surface subject to bacterial degradation.

A composition may be indirectly placed into contact with the food surface by applying the composition to food packaging materials or casings and thereafter applying the packaging to the food surface.

The preservatives may be added to the food substance by any suitable method, as for example, by blending or mixing, by spraying or misting a suspension of the bacteria and a suitable carrier onto the surface of the food, and the like. For example, the preservatives could be incorporated into an emulsion containing batter and a meat mixture, prior to further processing, such as stuffing and/or cooking.

It is intended that the invention should not be limited to a type of food, the stage of processing the food or its ingredients, or to the method or timing of applying the preservatives.

As used herein, fresh meat products refer to raw or uncooked meat (stored under refrigerated conditions) that may or may not contain additional spice mixtures, and includes integral or ground meat. Processed meat products refer to meats that have been i) formulated and cooked; ii) cured; or iii) uncured to produce a marketable product.

As used herein, predicted storage life refers to the capability of controlling spoilage for a discrete period, at which point spoilage becomes evident. For example, bacteria can be applied to a food product to attain a storage life of about 10 weeks or greater, at which point spoilage may be detectable. Within the 10-week storage period, the composition of the present invention controls spoilage by one or more of the following ways: i) by applying bacteria having a known time to spoilage; ii) by applying bacteria that produce one or more proteins or bacteriocins that kill or control spoilage bacteria; or iii) by combinations thereof.

This invention teaches that by combination of treatments, even with a reduced level of NaL/NaAc than is usual in commercial use, there is enhanced inhibition of *Listeria* compared with either method used alone.

For example, the inventors have found that for a food batter, a second preservative comprising a dried preparation of a *Carnobacterium* species and its dried fermentate has certain benefits in the production of a food product. See Example 5.

VI. EXAMPLES

Example 1

An experiment was initiated in which a second preservative (Micocin II) comprising a freeze dried preparation of CB1 and its dried fermentate was compared with other inhibitory technologies for the inhibition of *Listeria monocytogenes* on vacuum-packaged wieners.

Figure 2:
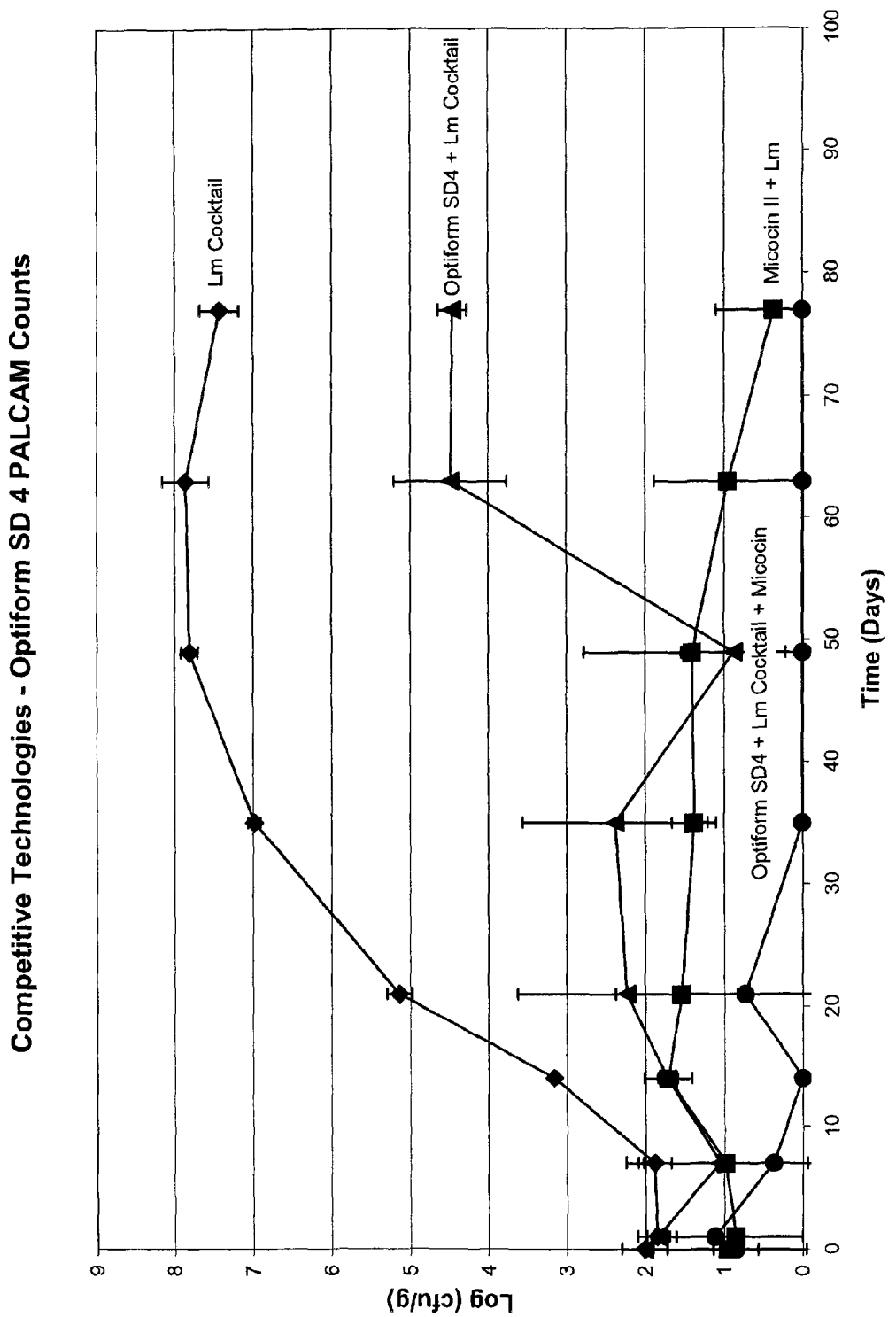
Figure 3:
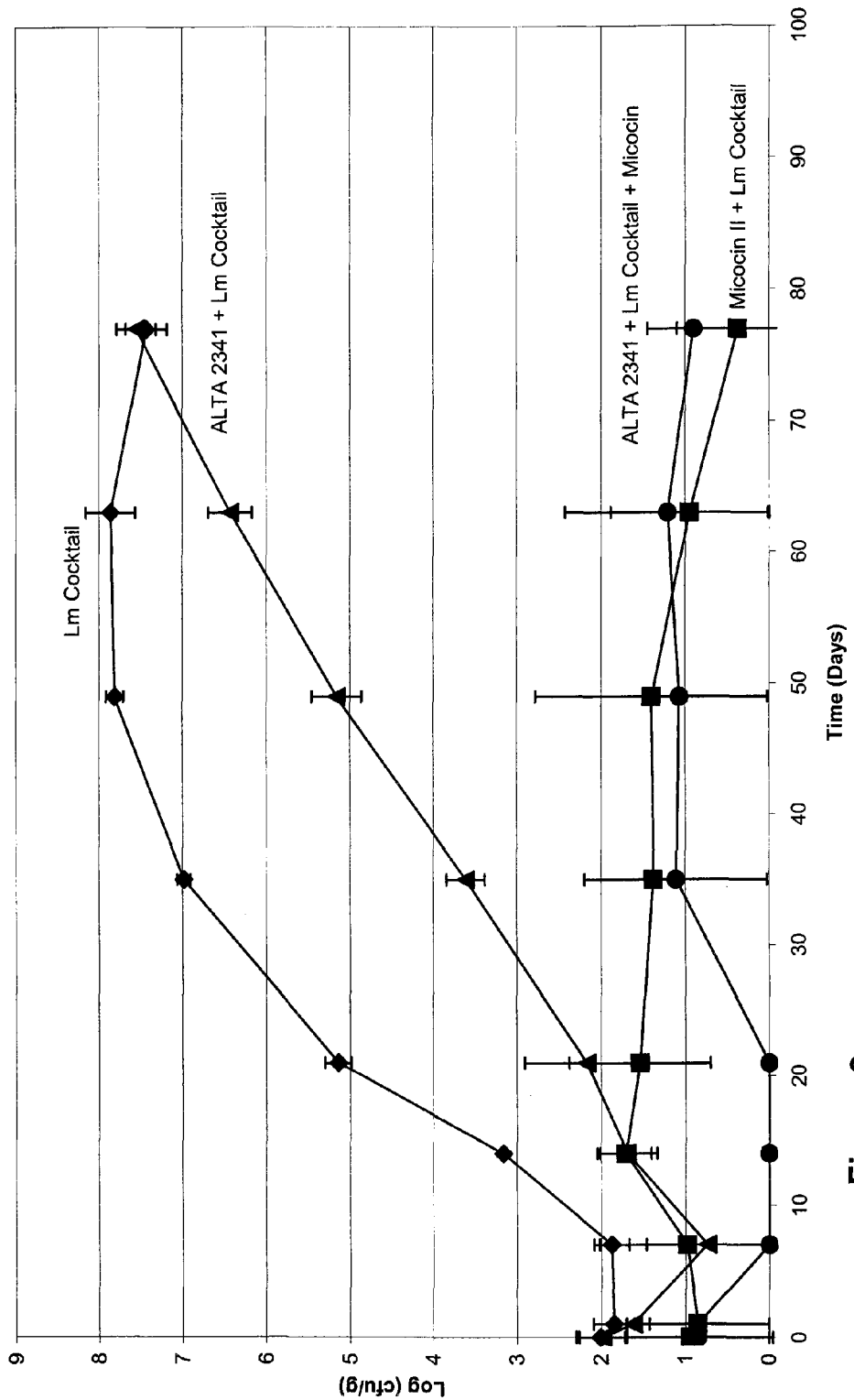

The objective of this study was to compare the efficacy of the second preservative with Na lactate (Galaflow 4.8% final conc.), NaL/NaAc mixture (Optiform 3.0% final conc.) and Alta 2341 (Kerry 3.0% final conc.). Based on this wiener formulation, it appeared that the second preservative performed as well as Galaflow and outperformed Optiform and Alta™ 2341. At the level of use of NaL (Galaflow) it is expected that the sensory quality of the wieners would be impaired. See data attached. The wiener formulation used was based on products manufactured in Canada. Results are shown graphically in FIGS. 1-3.

Example 2

Because the second preservative is approved for use in the United States we modified and repeated the study with a wiener formulation that represented a U.S. product. At the same time we also tested the efficacy of half the level of NaL/NaAc.

Because NaL/NaAc is the norm as a preservative for wieners produced in the U.S. it was decided to compare its efficacy at a commercially used level of 2.0% lactate and 0.1% Na diacetate and at one-half of those levels.

An experiment in which three replicates of the study were performed with product produced in the Griffith Laboratories pilot plant in Toronto Ontario Canada was initiated.

They were surface inoculated with a cocktail of four serovars of *L. monocytogenes* and, where required by the experimental design, with a level of second preservative identified as 3 AU (arbitrary units) that is 4.26 g second preservative per 100 mL sterile water.

Inoculated and control product was vacuum-packaged, stored at 4° C. and sampled by standard and enrichment bacterial enumeration and detection techniques over a time period of a minimum of 71 days.

For the challenge study, two wieners were placed aseptically into high oxygen barrier film bags (UniPac, Edmonton).

The *Listeria* cocktail consisted of one compatible strain from each of the following serovars: 1/2a. 1/2b, 3a and 4b was prepared by subculturing each of the strains on two occasions at 37° C. from frozen stock cultures in TSBYE (Difco Tryptic Soy Broth with 6% Yeast Extract) and 1 ml of each *Listeria* strain was placed in a 15 ml sterile Falcon tube, mixed vigorously on a vortex and centrifuged at 5000×g for 15 min. The supernatant was discarded and the cells were resuspended in 4 ml of sterile, 0.85% saline solution and diluted with 0.85% saline to approximately $10^5$ cfu of the *Listeria* strains per ml. Two 50 μl volumes were inoculated onto each side of the wieners and the wieners in the package were massaged vigorously by hand for 15 s.

The treatments inoculated with the second preservative were prepared by dissolving 4.26 g per 100 ml (3 AU) of sterile water tempered to 4° C. and 0.132 μl of the second preservative suspension was added to each side of the wieners and massaged vigorously. Inoculated wieners were vacuum packaged without delay and stored at 4° C.

Samples were withdrawn from storage at specified sampling intervals and tested for total bacterial load (APT), *Listeria* (PALCAM) counts and Carnobacteria (CTSI) by surface plating dilutions from 100 ml of sterile 0.1% peptone added to each of 3 packages after mixing of package contents.

If the *L. monocytogenes* count was undetectable on PALCAM, then at the next sampling period, one ml of sample was inoculated into 9 ml of UVM Modified *Listeria* Enrichment Broth. Inoculated tubes were placed at 37° C. and streaked onto PALCAM agar to detect *Listeria* spp. survivors after 24 and 48 h.

Figure 4:
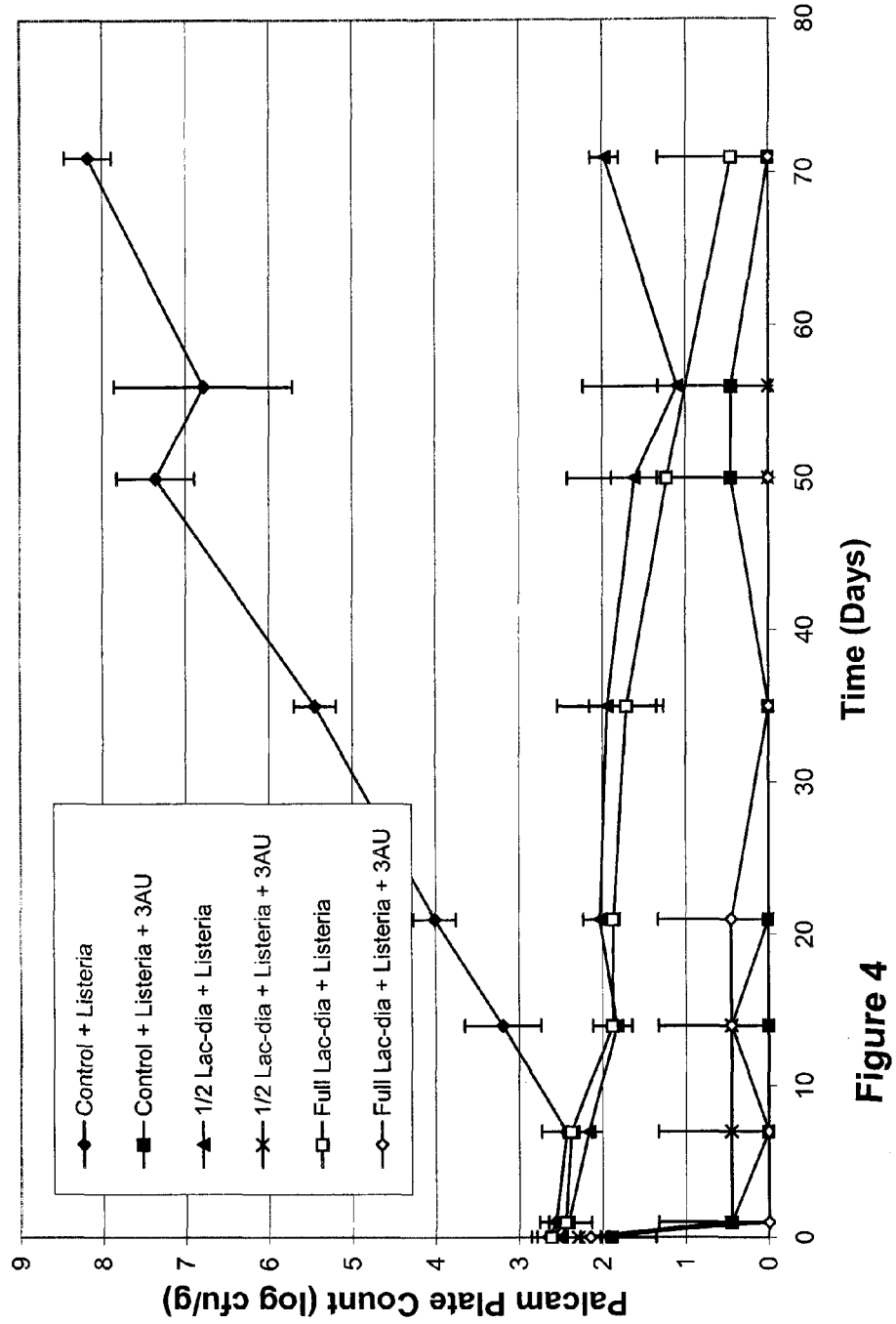
FIG. 4 shows the results of the experiments described in Example 2.

Results are shown graphically in FIG. 4.

Example 3

With these combinations, a cocktail of *L. monocytogenes* applied to the surface of wieners at approx. 80,000 cfu/package were reduced to an exceptional level compared with either treatment alone, soon after manufacture and up to 70 days of storage at 4° C. Results are shown in FIG. 4.

Example 4

The experiments in examples 1-3 were so successful in treating *Listeria* with the combined preservatives of the present invention that *Listeria* could not be detected by standard microbiological plating techniques. Therefore, in this example an enrichment step was added to determine if any *Listeria* was present. Table 1 shows that even with enrichment, a statistically significant number of test samples contained no detectable *Listeria* cells. The Table also shows that no detectable levels of *Listeria* were found for 71 days, a period that exceeds the shelf life of many food products.

TABLE 1

Competitive Technology #1 - 1/2 Lactate - Diacetate (Enrichment Data)

| Treatment | 7 | 14 | 21 | 35 | 50 | 56 | 71 |
|---|---|---|---|---|---|---|---|
| Negative Control | − | − | − | − | − | − | − |
| Listeria Control | + | + | + | + | + | + | + |
| Listeria + Micocin II (3AU) | − − + | − + + | − + + | − + + | + + − | + + + | + + + |
| Listeria + Lactate-Diacetate (Full) | + + + | + + + | + + + | + + + | + + + | + + + | + + + |
| Listeria + Lactate-Diacetate (Half) | + + + | + + + | + + + | + + + | + + + | + + + | + + + |
| Listeria + Lactate-Diacetate (Full) + Micocin II (3AU) | − − − | − − − | − − − | − − − | − − − | na na na | − − − |
| Listeria + Lactate-Diacetate (Half) + Micocin II (3AU) | − + − | − − − | − − − | − − − | − − + | − − − | − − − |

Example 5

The two preservative combination of the present invention was also tested by adding them to a meat batter that was processed into a wiener formulation. In the experimental results illustrated in FIG. 5, *Listeria* alone, a *Carnobacterium* cell/fermentate mixture alone, and Optiform alone were compared to compositions that contained a constant amount of Optiform mixed with various concentrations of the cell/fermentate mixture.

All of the experiments that included the combination of the two preservatives produced statistically significant reductions in the detected level of *Listeria* as compared to no preservative or each of the preservatives alone. In FIG. 5, A corresponds to 0.05% cell/fermentate and Optiform; B corresponds to 0.1% cell/fermentate and Optiform; C corresponds to 0.5% cell/fermentate and Optiform; D corresponds to 1% cell/fermentate and Optiform; and E corresponds to 5% cell/fermentate and Optiform. As noted above, the same amount of Optiform was used in each of the experiments.

We claim:

1. A composition comprising a preservative combination consisting of:
   (a) a first preservative consisting of lactate and diacetate where the level of the combination of lactate and diacetate is from an amount effective in killing *Listeria* up to about 1% lactate and up to about 0.05% diacetate; and
   (b) a second preservative, said second preservative consisting of an effective amount of a composition selected from the group consisting of at least one *Carnobacterium* species selected from *Carnobacterium maltaromaticum* as deposited in the ATCC under Accession Nos. PTA-5313, PTA-5314, PTA-5315; a fermentate containing at least one bacteriocin produced by the *Carnobacterium* species; a fermentate derived from the *Carnobacterium* species; one or more partially or wholly purified bacteriocins produced by the *Carnobacterium* species; and combinations thereof.

2. A method of preparing food comprising contacting a food with an effective amount of a preservative combination consisting of: (a) a first preservative consisting of lactate and diacetate where the level of the combination of lactate and diacetate is from an amount effective in killing *Listeria* up to about 1% lactate and up to about 0.05% diacetate; and (b) a second preservative, said second preservative consisting of an effective amount of a composition selected from the group consisting of at least one *Carnobacterium* species selected from *Carnobacterium maltaromaticum* as deposited in the ATCC under Accession Nos. PTA-5313, PTA-5314, PTA-5315; a fermentate containing at least one bacteriocin produced by the *Carnobacterium* species; a fermentate derived from the *Carnobacterium* species; one or more partially or wholly purified bacteriocins produced by the *Carnobacterium* species; and combinations thereof.

3. The method of claim 2 wherein contacting a food comprises adding the composition to a food batter prior to cooking.

4. The method of claim 2 wherein contacting a food comprises applying the composition to a food surface after processing.

5. A method of treating *Listeria* comprising administering a preservative combination consisting of (a) a first preservative consisting of lactate and diacetate where the level of the combination of lactate and diacetate is from an amount effective in killing *Listeria* up to about 1% lactate and up to about 0.05% diacetate; and (b) a second preservative, said second preservative consisting of an effective amount of a composition selected from the group consisting of at least one *Carnobacterium* species selected from *Carnobacterium maltaromaticum* as deposited in the ATCC under Accession Nos. PTA-5313, PTA-5314, PTA-5315; a fermentate containing at least one bacteriocin produced by the *Carnobacterium* species; a fermentate derived from the *Carnobacterium* species; one or more partially or wholly purified bacteriocins produced by the *Carnobacterium* species; and combinations thereof.

6. The method of claim 5 wherein the lactate is sodium lactate and the diacetate is sodium diacetate.

7. A method of preparing a food comprising adding a preservative combination consisting of (a) a first preservative consisting of lactate and diacetate where the level of lactate is up to about 1% and the level of diacetate is up to about 0.05%; and (b) a second preservative to a recipe for food, said second preservative consisting of an effective amount of a composition selected from the group consisting of at least one *Carnobacterium* species selected from *Carnobacterium maltaromaticum* as deposited in the ATCC under Accession Nos. PTA-5313, PTA-5314, PTA-5315; a fermentate containing at least one bacteriocin produced by the *Carnobacterium* species; a fermentate derived from the *Carnobacterium* species; one or more partially or wholly purified bacteriocins produced by the *Carnobacterium* species; and combinations thereof.

8. The composition of claim 1 further comprising a fermentate containing at least one bacteriocin.

9. The composition of claim 2 further comprising a fermentate containing at least one bacteriocin.

10. The composition of claim 5 further comprising a fermentate containing at least one bacteriocin.

11. The composition of claim 7 further comprising a fermentate containing at least one bacteriocin.

* * * * *